US012699817B2

(12) United States Patent
Alabbad et al.

(10) Patent No.: US 12,699,817 B2
(45) Date of Patent: Aug. 4, 2026

(54) SYSTEM AND METHOD FOR MODELING A ROCK SAMPLE

(71) Applicant: SAUDI ARABIAN OIL COMPANY, Dhahran (SA)

(72) Inventors: Abrar Alabbad, Al-Jish (SA); Yazeed Altowairqi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 1196 days.

(21) Appl. No.: 17/648,038

(22) Filed: Jan. 14, 2022

(65) Prior Publication Data

US 2023/0229827 A1     Jul. 20, 2023

(51) Int. Cl.
 *G06F 30/20*          (2020.01)
 *G01N 23/083*         (2018.01)
 (Continued)

(52) U.S. Cl.
 CPC ........... *G06F 30/20* (2020.01); *G01N 23/083* (2013.01); *G01N 23/2255* (2013.01);
 (Continued)

(58) Field of Classification Search
 CPC .. G06F 30/20; G01N 23/083; G01N 23/2255; G01N 33/24; G01N 2223/04;
 (Continued)

(56) References Cited

U.S. PATENT DOCUMENTS

| | | |
|---|---|---|
| 8,938,045 B2 | 1/2015 | Dvorkin et al. |
| 9,152,745 B2 | 10/2015 | Glinsky |

(Continued)

OTHER PUBLICATIONS

Altowairqi, Y., et al., "Shale elastic property relationships as a function of total organic carbon content using synthetic samples", Journal of Petroleum Science and Engineering, ScienceDirect, Elsevier B.V., vol. 133, Jun. 2015, pp. 392-400 (9 pages).

(Continued)

*Primary Examiner* — Andre Pierre Louis
(74) *Attorney, Agent, or Firm* — Osha Bergman Watanabe & Burton LLP

(57)          ABSTRACT

A rock modeling method is disclosed. An effective rock property of a rock sample is determined based on a digital rock. Instead of upscaling rock properties, the digital rock is constructed by upscaling relationships and rock physics models of segmented rock materials. Relationships between different scalar, elastic, and petrophysical properties of different segmented rock materials are established at the high-resolution scale where the pore structure is resolved. These relationships are then applied to the same rock material at the macro-scale. Finally, the effective rock properties are computed using Darcy-like solver to get the final values at a representative rock volume. Embodiments allow for performing non-destructive fluid/solid substitution and other reproducible digital experiments to study control factors that affect these relationships within rocks. Accordingly, for unconventional reservoirs, organic matter porosity can be filled with organic matter (kerogen) to build a rock physics model based on kerogen maturity and pore size.

17 Claims, 7 Drawing Sheets

(51) Int. Cl.
    *G01N 23/2255*     (2018.01)
    *G01N 33/24*     (2006.01)
(52) U.S. Cl.
    CPC ......... *G01N 33/24* (2013.01); *G01N 2223/04* (2013.01); *G01N 2223/081* (2013.01); *G01N 2223/418* (2013.01); *G01N 2223/419* (2013.01); *G01N 2223/616* (2013.01)
(58) Field of Classification Search
    CPC ....... G01N 2223/081; G01N 2223/418; G01N 2223/419; G01N 2223/616
    USPC .......................................................... 703/6
    See application file for complete search history.

(56)           References Cited

U.S. PATENT DOCUMENTS

| | | | |
|---|---|---|---|
| 9,201,026 B2 | 12/2015 | Walls et al. | |
| 9,372,162 B2 | 6/2016 | Ganz | |
| 9,507,047 B1 | 11/2016 | Dvorkin et al. | |
| 9,746,431 B2 | 8/2017 | Grader et al. | |
| 10,830,713 B2 | 11/2020 | Zhang | |
| 2010/0131204 A1* | 5/2010 | Dvorkin | G06T 7/0004 |
| | | | 702/6 |
| 2012/0221306 A1* | 8/2012 | Hurley | G01V 20/00 |
| | | | 703/6 |
| 2013/0259190 A1* | 10/2013 | Walls | G01N 23/046 |
| | | | 382/109 |
| 2013/0308831 A1* | 11/2013 | Dvorkin | G06T 7/0004 |
| | | | 382/109 |
| 2014/0044315 A1* | 2/2014 | Derzhi | G06T 15/08 |
| | | | 382/109 |
| 2017/0018073 A1* | 1/2017 | Sungkorn | G06F 18/24 |

OTHER PUBLICATIONS

Gerke, Kirill M., et al., "Universal Stochastic Multiscale Image Fusion: An Example Application for Shale Rock", Scientific Reports, DOI: 10.1038/srep15880, Nov. 2015, pp. 1-12 (12 pages).

Hao, Yue, et al., "Multiscale modeling of CO2-induced carbonate dissolution: From core to meter scale", International Journal of Greenhouse Gas Control, ScienceDirect, Elsevier Ltd., vol. 88, Jun. 2019, pp. 272-289 (18 pages).

Menke, H.P., et al., "Upscaling the porosity-permeability relationship of a microporous carbonate for Darcy-scale flow with machine learning", Scientific Reports, Nature Portfolio, vol. 11, No. 2625, 2021 (10 pages).

Moysey, Stephen, et al., "A framework for inferring field-scale rock physics relationships through numerical simulation", Geophysical Research Letters, vol. 32, No. L08304, DOI: 10.1029/2004GL022152, Apr. 2005, pp. 1-4 (4 pages).

Saxena, Nishank, et al., "Rock-physics models for heavy-oil and organic-solid substitution", The Leading Edge, Jun. 2016, pp. 506-510 (5 pages).

Sengupta, Mita, et al., "Quatifying the links between geochemical and geophysical properties of organic-rich carbonate mudrocks", The Leading Edge, Dec. 2019, pp. 914-922 (9 pages).

Siddiqui, Shameem and Aon A. Khamees, "Dual-Energy CT-Scanning Applications in Rock Characterization", SPE 90520, Society of Petroleum Engineers Inc., Sep. 2004, pp. 1-9 (9 pages).

Zhang, Feng, "A modified rock physics model of overmature organic-rich shale: application to anisotropy parameter prediction from well logs", Journal of Geophysics and Engineering, Oxford University Press, vol. 16, 2019, pp. 92-104 (13 pages).

Office Action issued by Saudi Arabian patent office for corresponding Saudi Arabian patent application No. 123441050, dated Aug. 28, 2024 (7 pages).

* cited by examiner

Sandstone Segment
302

302a

301a

Carbonate Segment
301

Sandstone Segment
302

Carbonate Segment
301

300

302b

301b

Computing
System
400

Output Device(s) ──408

404── Non-Persistent
Storage

Computer
Processor(s) ──402

406── Persistent
Storage

Communication
Interface ──412

Input Device(s) ──410

420

Network

422── Node X　· · ·　Node Y ──424

Client Device ──426

SYSTEM AND METHOD FOR MODELING A ROCK SAMPLE

BACKGROUND

Digital rocks are rock models for performing non-destructive, reproducible numeric experiments to understand what controls the physical and chemical processes of the rocks. The digital rocks are constructed based on 2-dimensional and/or 3-dimensional rock images, such as thin-section images, SEM, XRF, XRD, slapped core photograph, CT-scan, FIB-SEM, etc. The main objective of acquiring these images is to resolve the pore structure and heterogeneity of the rock at different scales in order to extract meaningful information about the rock for running numerical simulations. However, the measurement scale of these images may not be able to resolve the micro-pore structure in the rocks.

SUMMARY

In general, in one aspect, the invention relates to a method for modeling a rock sample. The method includes assigning first rock property values of a first rock property to respective grid cells in a digital rock that represents the rock sample, wherein the first rock property values are derived from measurements of the rock sample at a macro-scale, identifying a first digital rock portion of the digital rock corresponding to a first rock material segment of the rock sample, generating, based on a first high-resolution image of a first representative portion of the first rock material segment, a first rock property relationship between the first rock property and a second rock property, wherein the second rock property is associated with a physical rock structure that is resolved in the first high-resolution image and is not resolved at the macro-scale, computing, based on the first rock property relationship and the first rock property values in the first digital rock portion, second rock property values of the second rock property for assigning to corresponding grid cells in the first digital rock portion, and determining, based at least on the second rock property values in the first digital rock portion, an effective value of the second rock property of the rock sample.

In general, in one aspect, the invention relates to a computer system for modeling a rock sample. The system includes an analysis engine configured to identify a first digital rock portion of the digital rock corresponding to a first rock material segment of the rock sample, generate, based on a first high-resolution image of a first representative portion of the first rock material segment, a first rock property relationship between a first rock property and a second rock property, wherein the second rock property is associated with a physical rock structure that is resolved in the first high-resolution image and is not resolved at a macro-scale, and a modeling engine configured to assign first rock property values of the first rock property to respective grid cells in a digital rock that represents the rock sample, wherein the first rock property values are derived from measurements of the rock sample at the macro-scale, compute, based on the first rock property relationship and the first rock property values in the first digital rock portion, second rock property values of the second rock property for assigning to corresponding grid cells in the first digital rock portion, and determine, based at least on the second rock property values in the first digital rock portion, an effective value of the second rock property of the rock sample.

In general, in one aspect, the invention relates to a non-transitory computer readable medium (CRM) storing a digital rock for modeling a rock sample. The digital rock includes a plurality of grid cells corresponding to a plurality of locations in the rock sample, first rock property values of a first rock property assigned to respective grid cells in the digital rock, wherein the first rock property values are derived from measurements of the rock sample at a macro-scale, and a first digital rock portion corresponding to a first rock material segment of the rock sample, wherein a first rock property relationship between the first rock property and a second rock property is generated based on a first high-resolution image of a first representative portion of the first rock material segment, wherein the second rock property is associated with a physical rock structure that is resolved in the first high-resolution image and is not resolved at the macro-scale, wherein second rock property values of the second rock property are computed, based on the first rock property relationship and the first rock property values in the first digital rock portion, for assigning to corresponding grid cells in the first digital rock portion, and wherein an effective value of the second rock property of the rock sample is determined based at least on the second rock property values in the first digital rock portion.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1A:
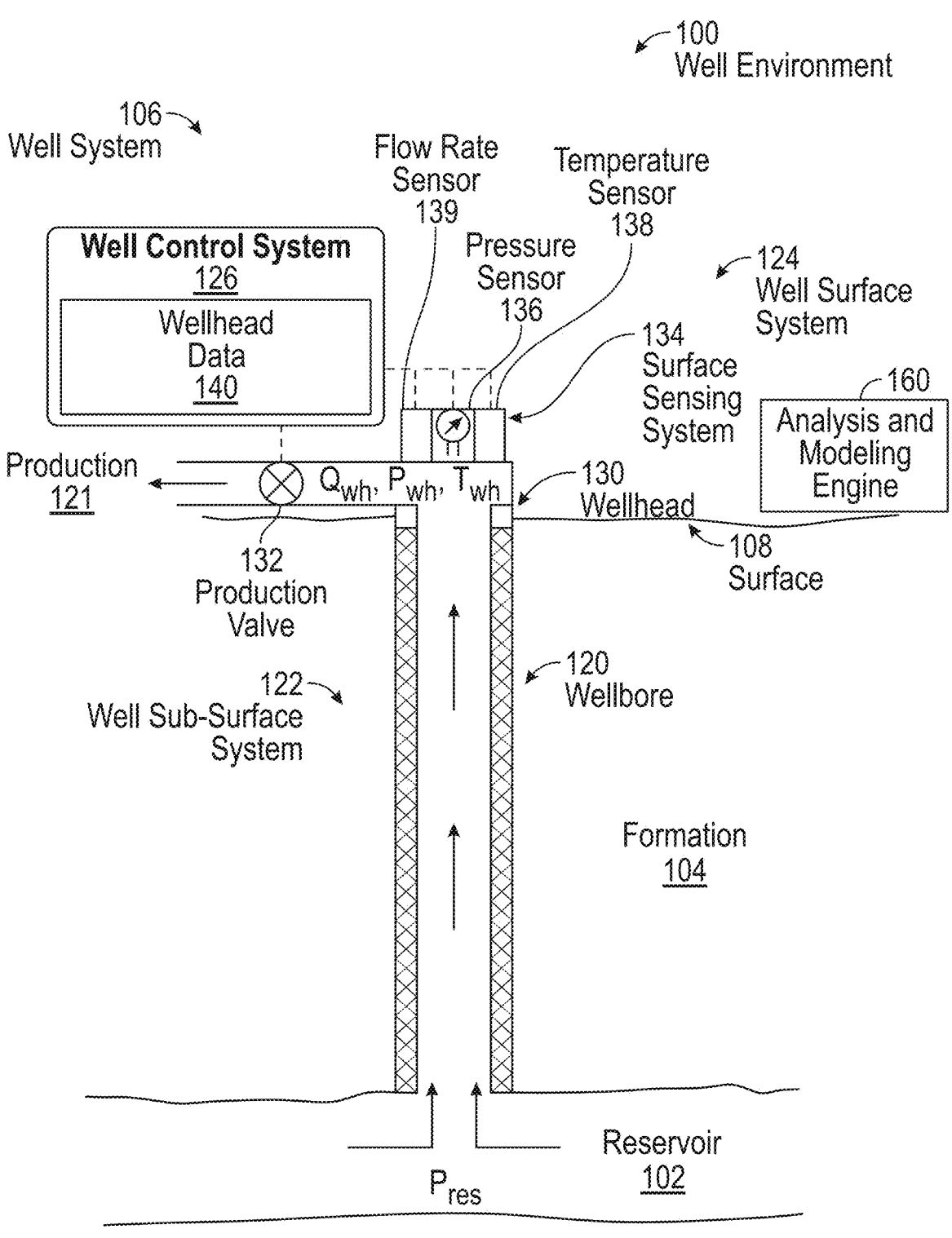
FIGS. 1A and 1B show systems in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method, a system, and a non-transitory computer readable medium for modeling a rock sample. In one or more embodiments of the invention, an effective rock property of the rock sample is determined based on a digital rock. Instead of upscaling rock properties, the digital rock is constructed by upscaling relationships and rock physics models of segmented rock materials. Relationships between different scalar, elastic, and petrophysical properties of different segmented rock materials are established at the high-resolution scale where the pore structure is resolved. These relationships are then applied to the same rock material at the macro-scale. Finally, the effective rock properties are computed using Darcy-like solver to get the final values at a representative rock volume. Embodiments allow for performing non-destructive fluid/ solid substitution and other reproducible digital experiments to study control factors that affect these relationships within rocks. Accordingly, for unconventional reservoirs, organic matter porosity can be filled with organic matter (kerogen) to build a rock physics model based on kerogen maturity and pore size.

FIG. 1A shows a schematic diagram in accordance with one or more embodiments. More specifically, FIG. 1A illustrates a well environment (100) that includes a hydrocarbon reservoir ("reservoir") (102) located in a subsurface formation ("formation") (104) and a well system (106). The formation (104) may include a porous formation that resides underground, beneath the Earth's surface ("surface") (108). In the case of the well system (106) being a hydrocarbon well, the reservoir (102) may include a portion of the formation (104). The formation (104) and the reservoir (102) may include different layers (referred to as subterranean intervals or geological intervals) of rock having varying characteristics, such as varying degrees of permeability, porosity, capillary pressure, and resistivity. In other words, a subterranean interval is a layer of rock having consistent permeability, porosity, capillary pressure, resistivity, and/or other characteristics. In the case of the well system (106) being operated as a production well, the well system (106) may facilitate the extraction of hydrocarbons (or "production") from the reservoir (102).

In some embodiments, the well system (106) includes a wellbore (120), a well sub-surface system (122), a well surface system (124), and a well control system ("control system") (126). The control system (126) may control various operations of the well system (106), such as well production operations, well completion operations, well maintenance operations, and reservoir monitoring, assessment and development operations. In some embodiments, the control system (126) includes a computer system that is the same as or similar to that of computer system (400) described below in FIGS. 4A and 4B and the accompanying description.

The wellbore (120) may include a bored hole that extends from the surface (108) into a target zone (i.e., a subterranean interval) of the formation (104), such as the reservoir (102). An upper end of the wellbore (120), terminating at or near the surface (108), may be referred to as the "up-hole" end of the wellbore (120), and a lower end of the wellbore, terminating in the formation (104), may be referred to as the "down-hole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the formation (104) or the reservoir (102) during injection operations, or the communication of monitoring devices (e.g., logging tools) into the formation (104) or the reservoir (102) during monitoring operations (e.g., during in situ logging operations).

In some embodiments, during operation of the well system (106), the control system (126) collects and records wellhead data (140) for the well system (106). The wellhead data (140) may include, for example, a record of measurements of wellhead pressure ($P_{wh}$) (e.g., including flowing wellhead pressure), wellhead temperature ($T_{wh}$) (e.g., including flowing wellhead temperature), wellhead production rate ($Q_{wh}$) over some or all of the life of the well (106), and water cut data. In some embodiments, the measurements are recorded in real-time, and are available for review or use within seconds, minutes, or hours of the condition being sensed (e.g., the measurements are available within 1 hour of the condition being sensed). In such an embodiment, the wellhead data (140) may be referred to as "real-time" wellhead data (140). Real-time wellhead data (140) may enable an operator of the well (106) to assess a relatively current state of the well system (106), and make real-time decisions regarding development of the well system (106) and the reservoir (102), such as on-demand adjustments in regulation of production flow from the well.

In some embodiments, the well sub-surface system (122) includes casing installed in the wellbore (120). For example, the wellbore (120) may have a cased portion and an uncased (or "open-hole") portion. The cased portion may include a portion of the wellbore having casing (e.g., casing pipe and casing cement) disposed therein. The uncased portion may include a portion of the wellbore not having casing disposed therein. In embodiments having a casing, the casing defines a central passage that provides a conduit for the transport of tools and substances through the wellbore (120). For example, the central passage may provide a conduit for lowering logging tools into the wellbore (120), a conduit for the flow of production (121) (e.g., oil and gas) from the reservoir (102) to the surface (108), or a conduit for the flow of injection substances (e.g., water) from the surface (108) into the formation (104). In some embodiments, the well sub-surface system (122) includes production tubing installed in the wellbore (120). The production tubing may provide a conduit for the transport of tools and substances through the wellbore (120). The production tubing may, for example, be disposed inside casing. In such an embodiment, the production tubing may provide a conduit for some or all of the production (121) (e.g., oil and gas) passing through the wellbore (120) and the casing.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures (called "wellhead casing hanger" for casing and "tubing hanger" for production tubing) for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more production valves (132) that are operable to control the flow of production (121). For example, a production valve (132) may be fully opened to enable unrestricted flow of production (121) from the wellbore (120), the production valve (132) may be partially opened to partially restrict (or "throttle") the flow of production (121) from the wellbore (120), and production valve (132) may be fully closed to fully restrict (or "block") the flow of production (121) from the wellbore (120), and through the well surface system (124).

In some embodiments, the wellhead (130) includes a choke assembly. For example, the choke assembly may include hardware with functionality for opening and closing the fluid flow through pipes in the well system (106). Likewise, the choke assembly may include a pipe manifold that may lower the pressure of fluid traversing the wellhead. As such, the choke assembly may include set of high pressure valves and at least two chokes. These chokes may be fixed or adjustable or a mix of both. Redundancy may be provided so that if one choke has to be taken out of service, the flow can be directed through another choke. In some embodiments, pressure valves and chokes are communicatively coupled to the well control system (126). Accordingly, a well control system (126) may obtain wellhead data regarding the choke assembly as well as transmit one or more commands to components within the choke assembly in order to adjust one or more choke assembly parameters.

Keeping with FIG. 1A, in some embodiments, the well surface system (124) includes a surface sensing system (134). The surface sensing system (134) may include sensors for sensing characteristics of substances, including production (121), passing through or otherwise located in the well surface system (124). The characteristics may include, for example, pressure, temperature and flowrate of production (121) flowing through the wellhead (130), or other conduits of the well surface system (124), after exiting the wellbore (120).

In some embodiments, the surface sensing system (134) includes a surface pressure sensor (136) operable to sense the pressure of production (121) flowing through the well surface system (124), after it exits the wellbore (120). The surface pressure sensor (136) may include, for example, a wellhead pressure sensor that senses a pressure of production (121) flowing through or otherwise located in the wellhead (130). In some embodiments, the surface sensing system (134) includes a surface temperature sensor (138) operable to sense the temperature of production (121) flowing through the well surface system (124), after it exits the wellbore (120). The surface temperature sensor (138) may include, for example, a wellhead temperature sensor that senses a temperature of production (121) flowing through or otherwise located in the wellhead (130), referred to as "wellhead temperature" ($T_{wh}$). In some embodiments, the surface sensing system (134) includes a flowrate sensor (139) operable to sense the flowrate of production (121) flowing through the well surface system (124), after it exits the wellbore (120). The flowrate sensor (139) may include hardware that senses a flowrate of production (121) ($Q_{wh}$) passing through the wellhead (130).

In some embodiments, the well system (106) includes an analysis and modeling engine (160). For example, the analysis and modeling engine (160) may include hardware and/or software with functionality for generating one or more reservoir models regarding the hydrocarbon-bearing formation (104) and/or performing one or more reservoir simulations. For example, the analysis and modeling engine (160) may store well logs and data regarding core samples for performing simulations. A reservoir simulator may further analyze the well log data, the core sample data, seismic data, and/or other types of data to generate and/or update the one or more reservoir models. While the analysis and modeling engine (160) is shown at a well site, embodiments are contemplated where reservoir simulators are located away from well sites. In some embodiments, the analysis and modeling engine (160) may include a computer system that is similar to the computer system (900) described below with regard to FIGS. 4A and 4B and the accompanying description.

Figure 1B:
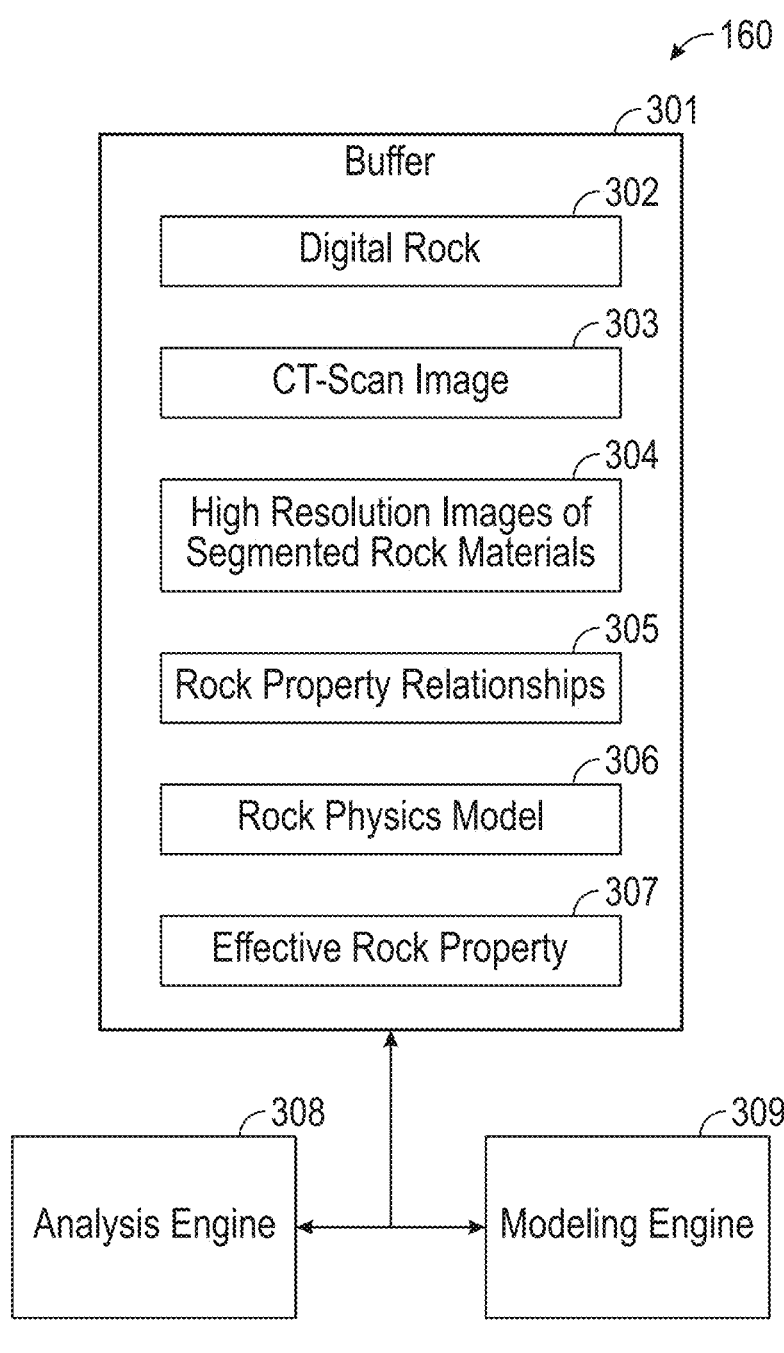

Turning to FIG. 1B, FIG. 1B shows a schematic diagram in accordance with one or more embodiments. Specifically, FIG. 1B illustrates details of the analysis and modeling engine (160) depicted in FIG. 1A above. In one or more embodiments, one or more of the modules and/or elements shown in FIG. 1B may be omitted, repeated, and/or substituted. Accordingly, embodiments of the invention should not be considered limited to the specific arrangements of modules and/or elements shown in FIG. 1B.

As shown in FIG. 1B, the analysis and modeling engine (160) has multiple components, including, for example, a buffer (301), an analysis engine (308), and a modelling engine (309). Each of these components (301, 308, 309) may be implemented in hardware (i.e., circuitry), software, or any combination thereof. Further, each of these components (301, 308, 309) may be located on the same computing device (e.g., personal computer (PC), laptop, tablet PC, smart phone, multifunction printer, kiosk, server, etc.) or on different computing devices connected by a network of any size having wired and/or wireless segments. In one or more embodiments, these components may be implemented using the computing system (400) described below in reference to FIGS. 4A and 4B. Each of these components is discussed below.

In one or more embodiments of the invention, the buffer (301) is configured to store a digital rock (302), a computed tomography scan (CT-scan) image (303), high-resolution images of segmented rock materials (304), rock property relationships (305), a rock physics model (306), and an effective rock property (307). The digital rock (302) is a computer model representing one or more physical properties (referred to as the rock properties) of a physical rock sample. The digital rock (302) includes grid cells each assigned with one or more data values to represent the one or more physical properties of the rock at a corresponding location within the rock sample. The digital rock (302) includes one or more digital rock portions each corresponding to a single rock material identified in the rock sample.

The CT-scan image (303) is an image of the rock sample, or a portion of the rock sample, acquired using multi-energy X-ray scans. In the CT-scan image (303), the CT number is a calculated value reflecting the X-ray attenuation coefficient in an image voxel. Each image voxel in the CT-scan image (303) corresponds to a location within the rock sample.

The X-ray attenuation coefficient is a characteristic of the rock material and is used to identify one or more rock material segments in the rock sample. The high-resolution images of segmented rock materials (304) are images of rock material segments with a resolution that is sufficiently high to resolve a structure of the rock material associated with relevant rock properties. For example, the high-resolution images of segmented rock materials (304) may be Focused Ion Beam Scanning Electron Microscopy (FIB-SEM) images where pore network in the rock sample can be resolved. Rock property relationships (305) are derived relationships between two rock properties for the rock material segments. For example, the rock property relationships (305) may include a porosity-permeability relationship for each of the rock material segments in the rock sample.

The rock physics model (306) is a model describing rock property measurements at various locations in the rock sample. Due to spatial resolution limitations of laboratory equipment and/or wireline instruments used to generate the rock property measurements, the rock physics model (306) is based on a macro-scale, such as a millimeter scale. For example, the rock property measurements may correspond to locations that are one or more millimeters apart in the rock sample and the rock physics model (306) may include equations that relate one or more macro-scale measurements of the rock to related micro-scale properties.

The effective rock property (307) is a computed value of a rock property that cannot be easily measured at the macro-scale. For example, the effective rock property (307) may include an effective porosity that is computed by upscaling the porosity-permeability relationships derived from the FIB-SEM images to the macro-scale. The up-scaled porosity-permeability relationships are then applied to corresponding rock material segments in conjunction with the macro-scale rock physics model.

In one or more embodiments of the invention, the analysis engine (308) is configured to analyze the CT-scan image (303) to identify the rock material segments, and to analyze the high resolution images of segmented rock materials (304) to generate the rock property relationships (305). The modelling engine (309) is configured to upscale the rock property relationships (305) to the macro-scale to be applied to each rock material segment in conjunction with the rock physics model (306). The modelling engine (309) is further configured to compute the effective rock property (307) from individual upscaled results of the rock material segments.

In one or more embodiments, the analysis engine (308) and the modelling engine (309) perform the functions described above using the method workflow described in reference to FIG. 2 below. An example of performing the method workflow using the analysis engine (308) and the modelling engine (309) is described in reference to FIGS. 3A-3C below.

Although the analysis and modeling engine (160) is shown as having three components (301, 308, 309), in one or more embodiments of the invention, the analysis and modeling engine (160) may have more or fewer components. Furthermore, the functions of each component described above may be split across components or combined in a single component. Further still, each component (301, 308, 309) may be utilized multiple times to carry out an iterative operation.

Figure 2:
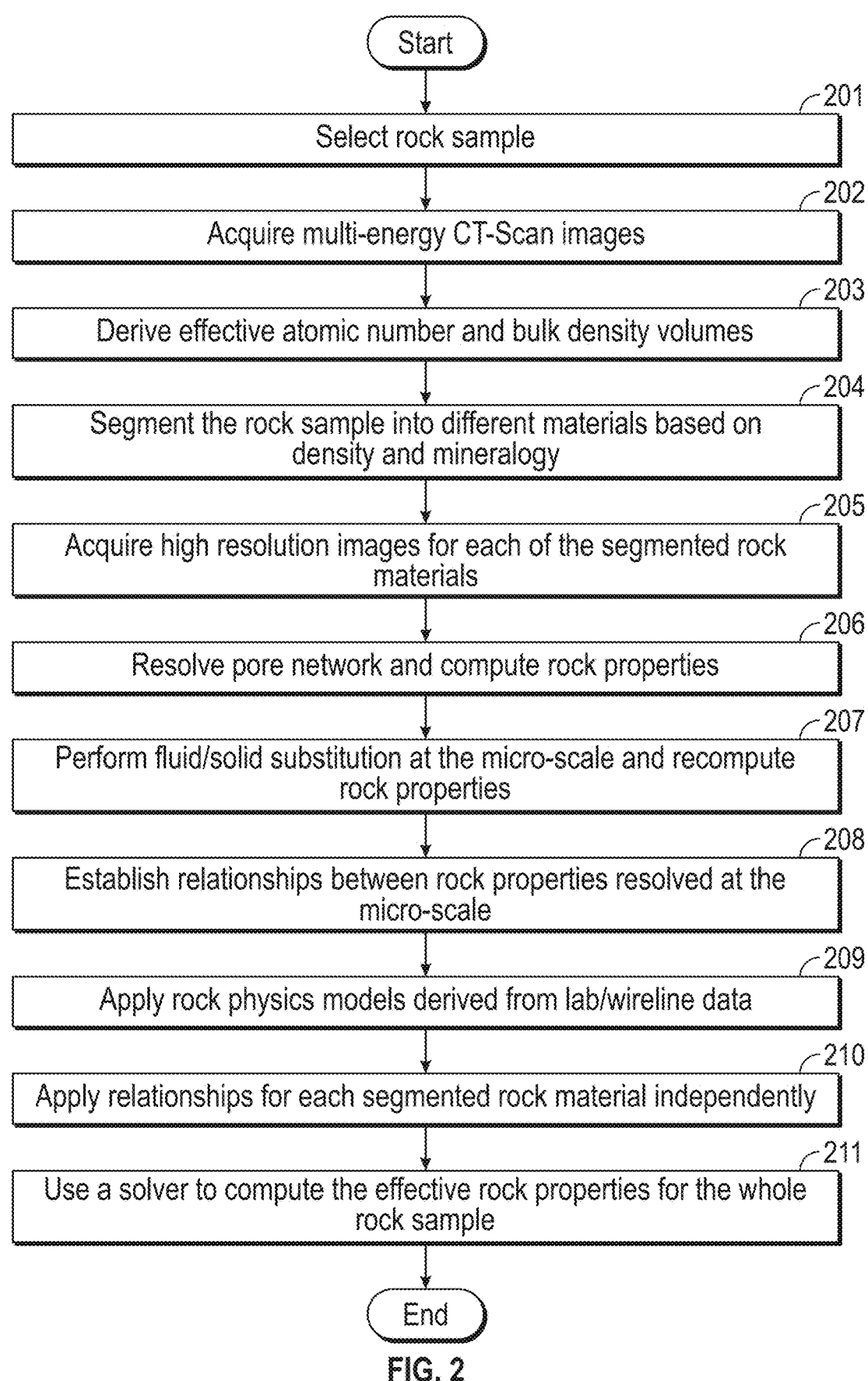
FIG. 2 shows a flowchart in accordance with one or more embodiments.

FIG. 2 shows a flowchart in accordance with one or more embodiments. One or more blocks in FIG. 2 may be performed using one or more components as described in FIGS. 1A-1B. While the various blocks in FIG. 2 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

As shown in FIG. 2, the flowchart presents a methodology to use multi-scale, multi-energy digital rock images in order to establish relationships between different rock properties and upscale the relationships to a representative scale. The methodology is based on rock properties being heterogenous at different geometric scales. In other words, the values of a rock property vary across different locations and exhibit different values at different sample sizes. For example, a porosity measurement computed from a high-resolution scale digital image to represent a porosity value corresponding to a few microns of the voxel dimension may not have the same value as a porosity measurement performed on a core plug that represents an average porosity value across a few millimeters resolved by the measurement instrument. However, relationships between two different rock properties hold at all scales.

For example, the porosity-permeability relationship derived from the high-resolution scale digital images is assumed to be the same as the porosity-permeability relationship derived from the core plug measurements. The methodology flowchart described below computes effective rock properties for the whole rock sample by independently applying this assumption to individual material segments identified in the rock sample. In other words, the porosity-permeability relationship derived from the high-resolution scale digital images is used to represent the porosity-permeability relationship at a macro-scale of the rock sample. Specifically, Blocks 201 through 208 compute rock properties at the high-resolution scale to establish relationships between related rock properties, and Blocks 209 through 211 apply the established relationships between related rock properties to individual material segments at a macro-scale.

Initially, in Block 201, a rock sample is selected. For example, the rock sample may be selected from cuttings retrieved in the drilling fluid of a well. In another example, the rock sample may be selected from core samples obtained by drilling using a hollow core drill. In particular, the rock sample is selected as a representative sample of an area of interest in a subterranean region, such as a reservoir or geological interval.

In Block 202, multi-energy computed tomography scan (CT-scan) images of the selected rock sample are acquired. The entire rock sample is scanned to generate the multi-energy CT-scan images. In an alternative scenario, a portion-of-interest of the rock sample may be scanned. For example, the multi-energy CT-scan images may be acquired using dual-energy X-ray scans at a nominal resolution (e.g., from 10 micron to 15 micron, 25 micron, 50 micron, etc.).

In Block 203, a data volume of effective atomic number and bulk density are derived from each multi-energy CT-scan image. The data volume is included in the digital rock representing the rock sample. In particular, each data pair of the effective atomic number and bulk density in the data volume is associated with an image voxel and the corresponding location within the rock sample. Each multi-energy CT-scan image voxel may correspond to one or more grid cells of the digital rock, and vice versa.

In Block 204, the rock sample is segmented into different material segments by analyzing the density and mineralogy information derived from the data volume. In particular, individual segments of the rock sample corresponding to different materials are identified in the digital rock. For example, the rock sample may include a sandstone segment, a siltstone segment, a carbonate segment, a quartz segment, etc. Correspondingly, the digital rock may include a sandstone digital rock potion, a siltstone digital rock potion, a carbonate digital rock potion, a quartz digital rock potion, etc.

In Block 205, high resolution images are acquired for each of the segmented rock materials. At least one high resolution image is acquired for a representative portion of each material segment. Each acquired image is used to represent the corresponding segmented rock material of the entire rock sample. For example, a sandstone high resolution image is used to represent the sandstone segment, a carbonate high resolution image is used to represent the carbonate segment, etc. For example, the high resolution images may be Focused Ion Beam Scanning Electron Microscopy (FIB- SEM) images acquired within each individual segment of the rock sample as identified in Block 204 above.

For porosity or permeability as the rock property of interest, the resolution of the FIB-SEM is selected based on the size of the smallest pores in the particular rock sample. For example, pore radii of coarse-grained sandstone and fine-grained sandstone range from 0.2 to >4 μm and 1 nm to 1.60 μm, respectively. Different resolutions of the FIB-SEM may be selected for different rock samples having different pore sizes. For other rock property of interest, e.g., Fracture width, pore throat (the narrowest part of the connection between two pores), and cementation thicknesses (natural recrystallized material), the resolution of the FIB-SEM is selected to resolve the smallest parts of rock sample based on the property of interest.

In Block 206, one or more pore network is resolved in each high resolution image to compute rock properties, such as porosity and permeability of the corresponding segmented rock material. For example, the porosity of each individual segmented rock material may be computed from the resolved pore networks using digital image segmentation algorithms, e.g., thresholding, or discontinuity/edge detection, or similarity detection. For example, the permeability of each individual segmented rock material may be computed from the resolved pore networks using finite element/finite difference/finite volume fluid flow simulation solution to NAvier-Stokes equation, capillary tube modeling (combining Darcy's law and the Hagen-Poiseuille equation), Lattice-Boltzmann method, and/or Kozeny-Carman permeability-porosity model. Specifically, the porosity and permeability are computed at the high-resolution scale for each high-resolution location in each material segment in the rock sample.

In Block 207, the rock properties, such as porosity and permeability of each segmented rock material is recomputed at the high-resolution scale using fluid/solid substitution method. For example, the rock frame material and pore filling material in the digital rock may be replaced by organic matter (kerogen) or water to study the effect of kerogen/water content on the seismic velocity. In one or more embodiments Block 207 is an optional step and may not be performed.

In Block 208, a relationship (e.g., porosity-permeability relationship) is established between rock properties resolved at the high-resolution scale for each segmented rock material. For example, a sandstone porosity-permeability relationship is established for the sandstone segment, a carbonate porosity-permeability relationship is established for the carbonate segment, etc. In particular, each porosity-permeability relationship includes a sequence of data pairs (i.e., porosity and permeability values) that are computed and recomputed using various methods described in Block 206, and fluid/solid substitution method above.

In Block 209, rock physics models derived from laboratory and/or wireline data are applied to the digital rock. For example, the rock physics model may include measured and/or derived permeability values at respective locations of the rock sample based on the laboratory and/or wireline data. Each location corresponds to a grid cell in the digital rock. By applying the rock physics model, the measured and/or derived permeability values are assigned to corresponding grid cells in the digital rock. In contrast to the high-resolution scale of the FIB-SEM image, the grid cell is based on the macro-scale due to the limitation of the laboratory instrument or wireline equipment. Because the pore network is not resolved at this macro-scale of the laboratory and/or wireline data, the aforementioned representative high resolution images are used to derive porosity values for assigning to grid cells in the digital rock.

In Block 210, the relationship between rock properties is independently applied to a corresponding digital rock portion for each segmented rock material. For example, the sandstone porosity-permeability relationship is applied to the sandstone digital rock portion, the carbonate porosity-permeability relationship is applied to the carbonate digital rock potion, etc. Specifically, the sandstone porosity-permeability relationship is used to compute the porosity value for each grid cell in the sandstone digital rock portion from the measured and/or derived permeability value assigned to the grid cell in Block 209 above. Similarly, the carbonate porosity-permeability relationship is used to compute the porosity value for each grid cell in the carbonate digital rock portion from the measured and/or derived permeability value assigned to the grid cell in Block 209 above. After independently applying porosity-permeability relationships to all corresponding digital rock portions, the digital rock is complete with both permeability values and porosity values representing the entire rock sample.

In Block 211, a solver (e.g., Darcy's law solver) is used to compute the effective rock properties for the entire rock sample. For example, the effective porosity value for the entire rock sample is computed using the Darcy's law solver over the digital rock. In one or more embodiments, the effective value of the second rock property is an acoustic velocity value, such as a seismic velocity value.

Figure 3A:
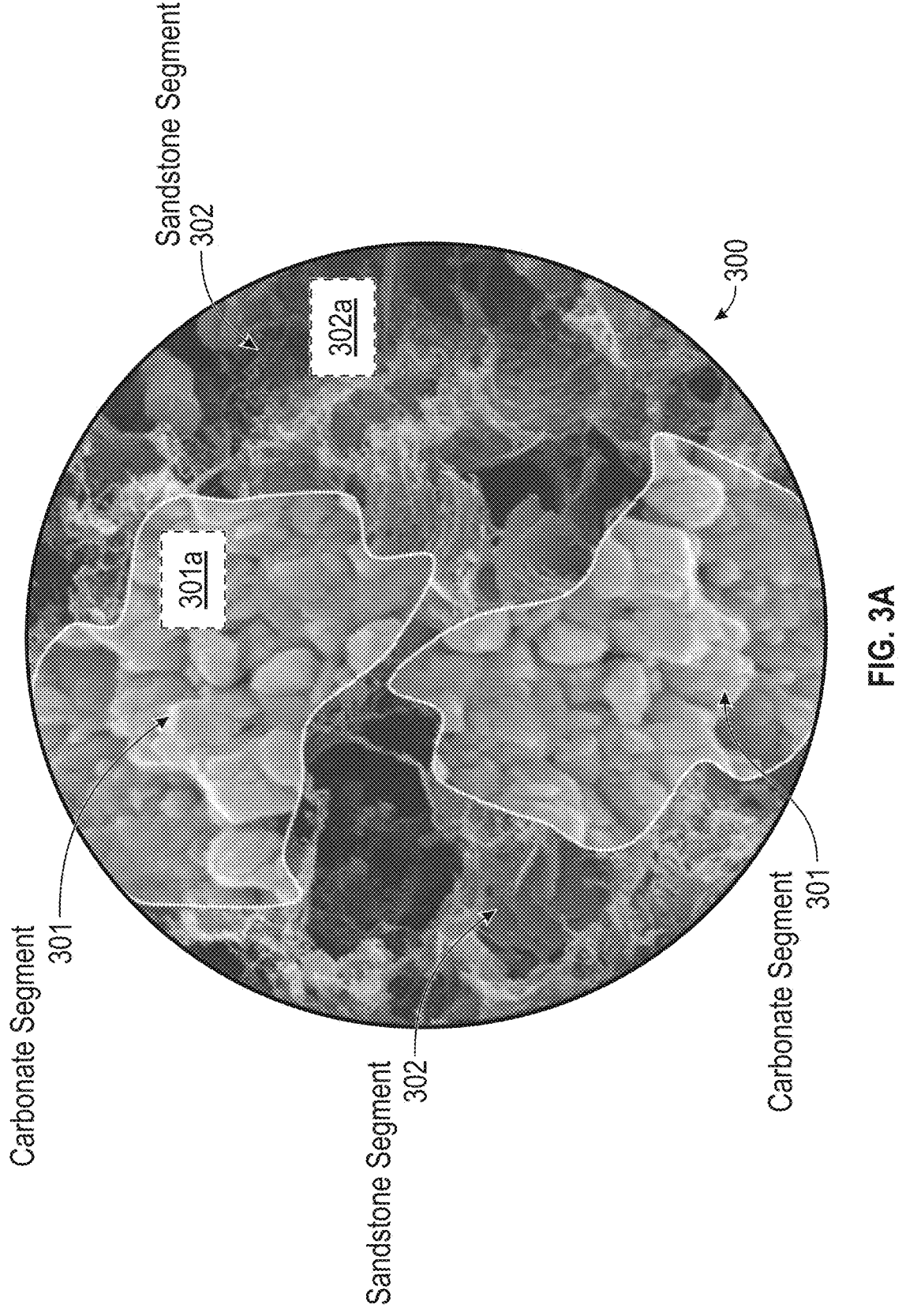
FIGS. 3A, 3B, and 3C show an example in accordance with one or more embodiments.

FIG. 3A shows an example multi-energy CT-scan image of a selected rock sample, as described in Blocks 201-202 of FIG. 2 above. As shown in FIG. 3A, the multi-energy CT-scan image shows a rock sample (300) that is divided into multiple segmented rock materials, such as the Carbonate segment (301), Sandstone segment (302), etc. In particular, a representative portion (301*a*) is identified in the Carbonate segment (301), and a representative portion (302*a*) is identified in the Sandstone segment (302). Although the Carbonate segment (301) and Sandstone segment (302) are schematically depicted as having irregular or less symmetrical physical shapes, the segmented rock materials may be elliptical in shape.

Figure 3B:
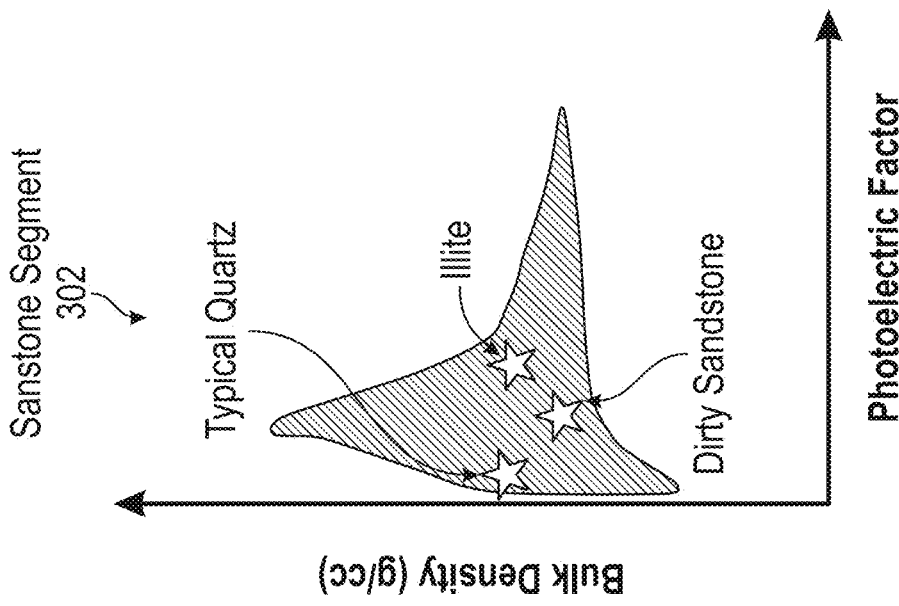
Figure 3B:
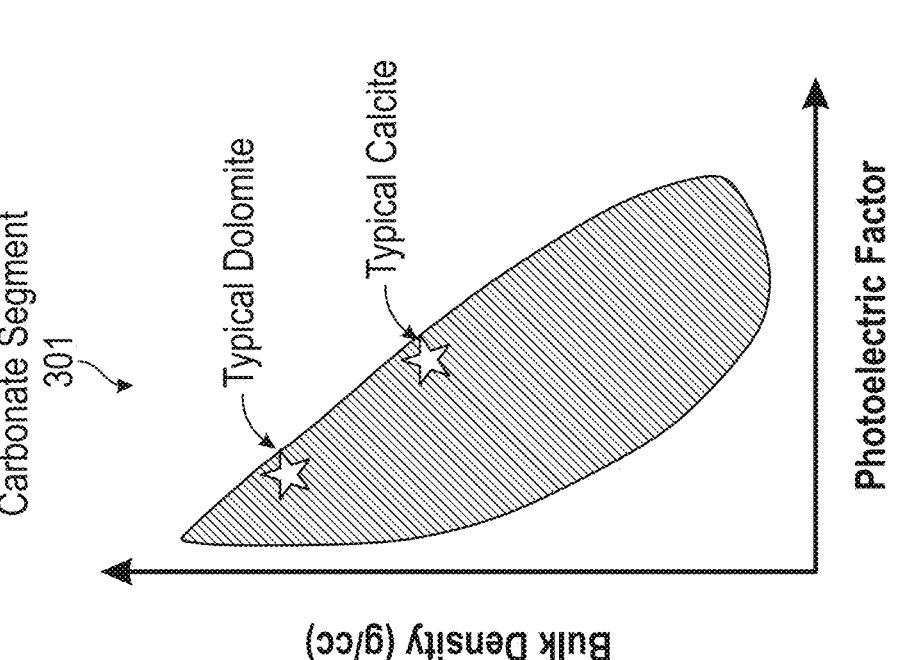

FIG. 3B shows the bulk density and mineralogy information derived from the data volume of the multi-energy CT-scan image depicted in FIG. 3A above. The bulk density and mineralogy information are used to identify the carbonate segments (301) and sandstone segments (302) in the rock sample, as described in Blocks 203-204 of FIG. 2 above. Specifically, FIG. 3B shows bulk density (measured in g/cc) versus photoelectric factor (measured in barns/electron) cross-plot for one sample of the carbonate segments and sandstone segments in the rock sample. For example, the carbonate segments (301) contain calcite and dolomite materials, while the sandstone segments (302) contain quartz, feldspar, chert, and mica materials.

Figure 3C:
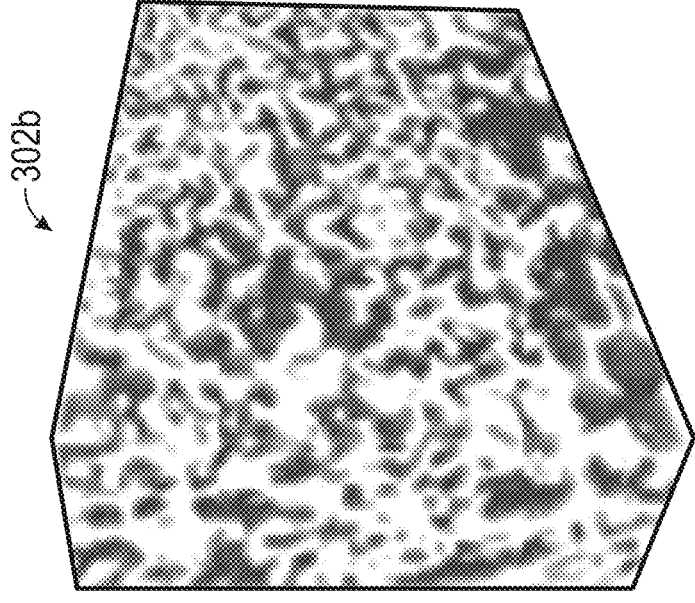
Figure 3C:
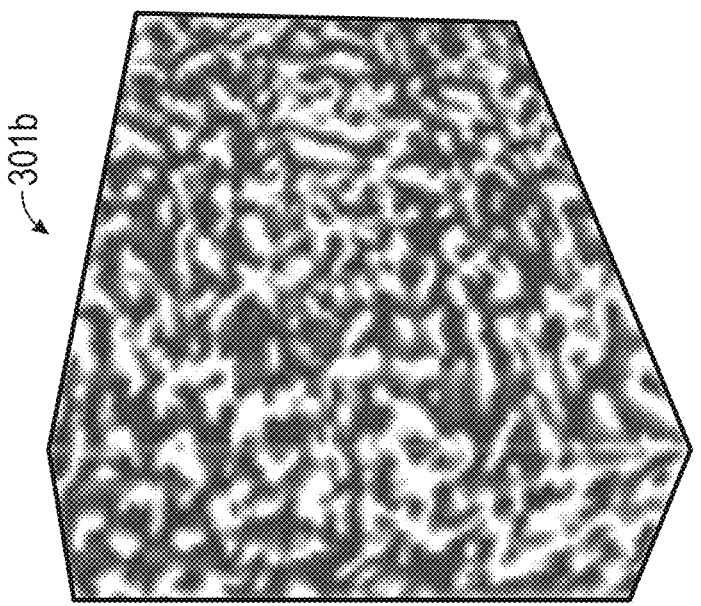

FIG. 3C shows example high resolution images are acquired for each of the segmented rock materials of the selected rock sample based on the example data volume depicted in FIG. 3B above, as described in Block 205 of FIG. 2 above. As shown in FIG. 3C, the high resolution image (301*b*) is a 3D FIB-SEM image of the representative portion (301*a*) of the Carbonate segment (301) depicted in FIG. 3A above. Similarly, the high resolution image (302*b*) is a 3D FIB-SEM image of the representative portion (302*a*) of the Sandstone segment (302) depicted in FIG. 3A above.

Figures 4A, 4B:
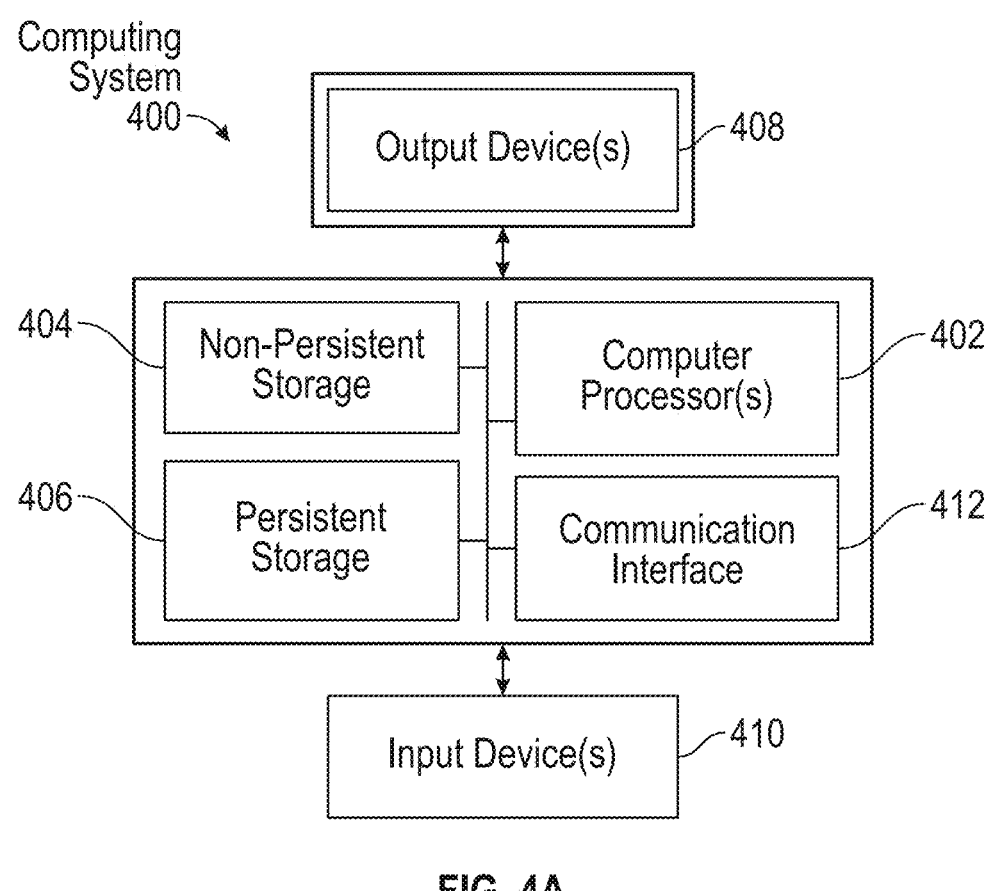
FIGS. 4A and 4B show a computing system in accordance with one or more embodiments.

Embodiments disclosed herein may be implemented on a computing system. Any combination of mobile device, desktop, server, router, switch, embedded device, or other types of hardware may be used. As shown in FIG. 4A, the computing system (400) may include one or more computer processors (402), non-persistent storage (404) (e.g., volatile memory, such as random access memory (RAM), cache memory), persistent storage (406) (e.g., a hard disk, an optical drive such as a compact disk (CD) drive or digital versatile disk (DVD) drive, a flash memory, etc.), a communication interface (412) (e.g., Bluetooth interface, infrared interface, network interface, optical interface, etc.), and numerous other elements and functionalities.

The computer processor(s) (402) may be an integrated circuit for processing instructions. For example, the computer processor(s) may be one or more cores or micro-cores of a processor. The computing system (400) may also include one or more input devices (410), such as a touchscreen, keyboard, mouse, microphone, touchpad, electronic pen, or any other type of input device.

The communication interface (412) may include an integrated circuit for connecting the computing system (400) to a network (not shown) (e.g., a local area network (LAN), a wide area network (WAN) such as the Internet, mobile network, or any other type of network) and/or to another device, such as another computing device.

Further, the computing system (400) may include one or more output devices (408), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (402), non-persistent storage (404), and persistent storage (406). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

The computing system (400) in FIG. 4A may be connected to or be a part of a network. For example, as shown in FIG. 4B, the network (420) may include multiple nodes (e.g., node X (422), node Y (424)). Each node may correspond to a computing system, such as the computing system shown in FIG. 4A, or a group of nodes combined may correspond to the computing system shown in FIG. 4A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (400) may be located at a remote location and connected to the other elements over a network.

Although not shown in FIG. 4B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (for example, node X (422), node Y (424)) in the network (420) may be configured to provide services for a client device (426). For example, the nodes may be part of a cloud computing system. The nodes may include functionality to receive requests from the client device (426) and transmit responses to the client device (426). The client device (426) may be a computing system, such as the computing system shown in FIG. 4A. Further, the client device (426) may include or perform all or a portion of one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

What is claimed is:

1. A method for modeling a rock sample, comprising:

drilling a well to obtain the rock sample;

assigning first rock property values of a first rock property to respective grid cells in a digital rock that represents the rock sample, wherein the first rock property values are derived from measurements of the rock sample at a macro-scale;

scanning, via a computed tomography (CT) scanner, the rock sample to obtain a multi-energy CT-scan image;

determining a data volume mineralogy and bulk density from the multi-energy CT-scan image;

identifying a first rock material segment of a plurality of rock material segments of the rock sample based on the data volume mineralogy and bulk density, wherein the first rock material segment comprises pores and grains of a single rock material;

identifying a first digital rock portion of the digital rock corresponding to the first rock material segment of the rock sample;

generating, using a Focused Ion Beam Scanning Electron Microscope, a first high-resolution image of a first representative portion of the first rock material segment;

generating, based on the first high-resolution image of a first representative portion of the first rock material segment, a first rock property relationship between the first rock property and a second rock property, wherein the second rock property is associated with a physical rock structure that is resolved in the first high-resolution image and is not resolved at the macro-scale;

computing, based on the first rock property relationship and the first rock property values in the first digital rock portion, second rock property values of the second rock property for assigning to corresponding grid cells in the first digital rock portion; and computing, for each grid cell in the first digital rock portion, a second rock property value of the second rock property based on the first rock property relationship and the first rock property values of the grid cell;

determining, based at least on the second rock property values in the first digital rock portion, an effective value of the second rock property of the rock sample; and producing hydrocarbons, via a production valve, from a production system based on the effective value of the second rock property of the rock sample.

2. The method of claim 1, wherein the first rock material segment forms a contiguous volume of the single rock material.

3. The method of claim 1, wherein generating the first rock property relationship comprises generating a value pair of the first rock property and the second rock property for each of a plurality of voxels in the first high-resolution image, wherein the first rock property relationship is generated based at least on the value pair for each of the plurality of voxels in the first high-resolution image.

4. The method of claim 1, further comprising:

identifying a second digital rock portion of the digital rock corresponding to a second rock material segment of the plurality of rock material segments of the rock sample based on the data volume mineralogy and bulk density;

generating, based on a second high-resolution image of a second representative portion of the second rock material segment, a second rock property relationship between the first rock property and the second rock property;

further computing, for each grid cell in the second digital rock portion, the second rock property value of the second rock property based on the second rock property relationship and the first rock property values of the grid cell of the second digital rock portion;

further computing, based on the second rock property relationship and the first rock property values in the second digital rock portion, the second rock property values of the second rock property for assigning to corresponding grid cells in the second digital rock portion; and further determining, based on the second rock property value for each grid cell in the second digital rock portion, the effective value of the second rock property of the rock sample.

5. The method of claim 2, wherein the plurality of rock material segments comprises one or more of a carbonate segment, a sandstone segment, a siltstone segment, and a quartz segment.

6. The method of claim 1, wherein the effective value of the second rock property comprises an acoustic velocity value.

7. A system for modeling a rock sample, comprising:

a computed tomography (CT) scanner configured to:

scan the rock sample to obtain a multi-energy CT-scan image;

an analysis engine comprising at least one processor configured to:

determine a data volume mineralogy and bulk density from the multi-energy CT-scan image, identify a first rock material segment of the rock sample based on the data volume mineralogy and bulk density, wherein the first rock material segment comprises pores and grains of a single rock material;

identify a first digital rock portion of the digital rock corresponding to the first rock material segment of the rock sample;

generate, using a Focused Ion Beam Scanning Electron Microscope, a first high-resolution image of a first representative portion of the first rock material segment; and generate, based on the first high-resolution image of a first representative portion of the first rock material segment, a first rock property relationship between a first rock property and a second rock property, wherein the second rock property is associated with a physical rock structure that is resolved in the first high-resolution image and is not resolved at a macro-scale; and a modeling engine configured to:

select the rock sample, from a well, received by drilling the well using a drilling system;

assign first rock property values of the first rock property to respective grid cells in a digital rock that represents the rock sample, wherein the first rock property values are derived from measurements of the rock sample at the macro-scale;

compute, for each grid cell in the first digital rock portion, a second rock property value of the second rock property based on the first rock property relationship and the first rock property values of the grid cell;

compute, based on the first rock property relationship and the first rock property values in the first digital rock portion, second rock property values of the second rock property for assigning to corresponding grid cells in the first digital rock portion;

determine, based at least on the second rock property values in the first digital rock portion, an effective value of the second rock property of the rock sample; and transmit, to a production system, signals determined from the effective value of the second rock property, and cause a production valve to produce hydrocarbons based on the effective value of the second rock property of the rock sample.

8. The system of claim 7, wherein the first rock material segment forms a contiguous volume of the single rock material.

9. The system of claim 7, wherein generating the first rock property relationship comprises generating a value pair of the first rock property and the second rock property for each of a plurality of voxels in the first high-resolution image, wherein the first rock property relationship is generated based at least on the value pair for each of the plurality of voxels in the first high-resolution image.

10. The system of claim 7, the analysis engine further configured to:

identify a second digital rock portion of the digital rock corresponding to a second rock material segment of the rock sample based on the data volume mineralogy and bulk density; and generate, based on a second high-resolution image of a second representative portion of the second rock material segment, a second rock property relationship between the first rock property and the second rock property, and the modeling engine further configured to:

further compute, for each grid cell in the second digital rock portion, based on the second rock property relationship and the first rock property values in the second digital rock portion, the second rock property values of the second rock property based on the second rock property relationship and the first rock property values of the grid cell in the second digital rock portion for assigning to corresponding grid cells in the second digital rock portion; and further determine, based on the second rock property value for each grid cell in the second digital rock portion, the effective value of the second rock property of the rock sample.

11. The system of claim 7, wherein the first rock material segment comprises one or more of a carbonate segment, a sandstone segment, a siltstone segment, and a quartz segment.

12. The system of claim 7, wherein the effective value of the second rock property comprises an acoustic velocity value.

13. A non-transitory computer readable medium (CRM) storing a digital rock for modeling a rock sample including computer-executable data executed by a processor to perform a method comprising the steps of:

drilling a well to obtain sample comprising a plurality of grid cells corresponding to a plurality of locations in the rock sample, the rock sample selected from the drilled well;

assigning first rock property values of a first rock property assigned to respective grid cells in the digital rock, wherein the first rock property values are derived from measurements of the rock sample at a macro-scale;

scanning, via computed tomography (CT) scanner, the rock sample to obtain a multi-energy computer tomography (CT) scan image of the rock sample, identifying a first rock material segment of the rock sample based on a data volume mineralogy and bulk density determined from the multi-energy CT scan image, wherein the first rock material segment comprises pores and grains of a single rock material;

identifying a first digital rock portion corresponding to the first rock material segment of the rock sample;

generating a first high-resolution image of a first representative portion of the first digital rock segment generated by a Focused Ion Beam Scanning Electron Microscope, generating a first rock property relationship between the first rock property and a second rock property based on the first high-resolution image of a first representative portion of the first rock material segment, wherein the second rock property is associated with a physical rock structure that is resolved in the first high-resolution image and is not resolved at the macro-scale, computing, for each grid cell in the first digital rock portion, a second rock property value of the second rock property, based on the first rock property relationship and the first rock property values of the grid cell in the first digital rock portion, for assigning to corresponding grid cells in the first digital rock portion, computing, for each grid cell in the first digital rock portion, a second rock property value of the second rock property based on the first rock property relationship and the first rock property values of the grid cell;

determining an effective value of the second rock property of the rock sample based at least on the second rock property values in the first digital rock portion, and producing hydrocarbons, via a production valve, from a production system based on the effective value of the second rock property of the rock sample.

14. The CRM of claim 13, wherein the first rock material segment forms a contiguous volume of the single rock material wherein a multi-energy computed tomography scan (CT-scan) image of the rock sample is analyzed to generate a data volume of effective atomic number and bulk density of the rock sample; and wherein a plurality of rock material segments of the rock sample is identified based on the data volume, and wherein the plurality of rock material segments comprise the first rock material segment.

15. The CRM of claim 13, wherein generating the first rock property relationship comprises generating a value pair of the first rock property and the second rock property for each of a plurality of voxels in the first high-resolution image, wherein the first rock property relationship is generated based at least on the value pair for each of the plurality of voxels in the first high-resolution image, and wherein the effective value of the second rock property comprises an acoustic velocity value.

16. The CRM of claim 13, the digital rock further comprising a second digital rock portion of the digital rock corresponding to a second rock material segment of the plurality of rock material segments of the rock sample;

wherein a second rock property relationship between the first rock property and the second rock property is generated based on a second high-resolution image of a second representative portion of the second rock material segment, wherein, for each grid cell in the second digital rock portion, the second rock property value of the second rock property is further computed, based on the second rock property relationship and the first rock property values of the grid cell in the second digital rock portion, for assigning to corresponding grid cells in the second digital rock portion, and wherein the effective value of the second rock property of the rock sample is further determined based on the second rock property value for each grid cell in the second digital rock portion.

17. The CRM of claim 13, wherein the plurality of rock material segments comprises one or more of a carbonate segment, a sandstone segment, a siltstone segment, and a quartz segment.

* * * * *